(12) United States Patent
Rayaprol

(10) Patent No.: US 11,654,208 B2
(45) Date of Patent: May 23, 2023

(54) DISINFECTING AND ILLUMINATING LIGHTING ASSEMBLIES

(71) Applicant: Rajasekhar Rayaprol, Warrenton, VA (US)

(72) Inventor: Rajasekhar Rayaprol, Warrenton, VA (US)

( * ) Notice: Subject to any disclaimer, the term of this patent is extended or adjusted under 35 U.S.C. 154(b) by 242 days.

(21) Appl. No.: 17/172,521

(22) Filed: Feb. 10, 2021

(65) Prior Publication Data

US 2021/0369888 A1 Dec. 2, 2021

Related U.S. Application Data

(60) Provisional application No. 63/030,709, filed on May 27, 2020.

(51) Int. Cl.
| | |
|---|---|
| *A61L 2/10* | (2006.01) |
| *A61L 2/26* | (2006.01) |
| *F21V 14/08* | (2006.01) |
| *F21V 9/30* | (2018.01) |

(52) U.S. Cl.
CPC ...... *A61L 2/10* (2013.01); *A61L 2/26* (2013.01); *F21V 9/30* (2018.02); *F21V 14/08* (2013.01); *A61L 2202/11* (2013.01); *A61L 2202/14* (2013.01)

(58) Field of Classification Search
CPC ..... A61L 2/10; A61L 2/22; F21V 9/30; F21V 9/32; F21V 9/40; F21V 9/45; F21V 14/08
See application file for complete search history.

(56) References Cited

U.S. PATENT DOCUMENTS

| | | | |
|---|---|---|---|
| 4,262,327 A | 4/1981 | Kovacik et al. | |
| 4,991,070 A | 2/1991 | Stob | |
| 9,360,195 B2 | 6/2016 | Goeckel et al. | |
| 2003/0076028 A1* | 4/2003 | Nieda | A01G 7/045 |
| | | | 313/485 |
| 2006/0261291 A1* | 11/2006 | Gardner, III | F21V 9/45 |
| | | | 250/504 R |
| 2016/0000019 A1 | 1/2016 | Koerner et al. | |

FOREIGN PATENT DOCUMENTS

| | | |
|---|---|---|
| JP | 2012250285 | 12/2012 |
| KR | 100926893 B1 | 11/2009 |

\* cited by examiner

*Primary Examiner* — Eliza W Osenbaugh-Stewart

(57) ABSTRACT

A lighting assembly includes a lightbulb, sleeve, motor assembly, a control circuit, power source, first state, and second state. The control circuit is communicatively coupled to the power source, the lightbulb, and the motor assembly. The lightbulb emits ultra violet ("UV") radiation. The sleeve converts UV radiation to visible light, is circumferentially positioned about the lightbulb, and is rotatably coupled to the lightbulb via the motor assembly. The motor assembly is mechanically coupled to the sleeve, and selectively rotates the sleeve about the lightbulb and thereby positions the lighting assembly in the first state or the second state. The sleeve includes a slit that emits the UV radiation from the lightbulb. In the first state, the lighting assembly emits UV radiation towards a surface. In the second state, the lighting assembly emits visible light towards the surface.

3 Claims, 17 Drawing Sheets

DISINFECTING AND ILLUMINATING LIGHTING ASSEMBLIES

CROSS-REFERENCE TO RELATED APPLICATIONS

This application claims priority to U.S. Provisional Application No. 63/030,709 filed May 27, 2020, which is hereby incorporated herein by reference.

FIELD OF THE INVENTION

The present disclosure relates generally to lighting assemblies. More specifically, the present disclosure describes disinfecting and illuminating lighting assemblies.

BACKGROUND OF THE INVENTION

With the onset of more deadly viruses and diseases such as COVID-19, it may be useful to set standards and equipment to sterilize constantly used surfaces and the air without having to manually clean them. With the SARS-CoV-2 virus, which is transmitted by airborne droplets, manual cleaning is not even possible. While there exists many precautions today such as with the use of sanitary wipes, antiviral sprays, and masks, it is still difficult to employ means of cleaning many surfaces simultaneously. Ultraviolet (UV) light has often been used to disinfect items and surfaces such as cleaning water for drinking to sterilizing science lab equipment to the use of UV emitting handheld devices waved over items such as a phone.

Fluorescent bulbs, which are readily available and often times already installed as a light fixture in places such as restaurants and department stores, produce UV light but this is not usable for disinfection. Disinfecting UV lightbulbs are also available, though less widely used, but these are not suitable for illumination. There exists a need in the art for lighting assemblies that that disinfect as well as illuminate.

BRIEF DESCRIPTION OF THE DRAWINGS

Some of the embodiments will be described in detail, with reference to the following figures, wherein like designations denote like members, wherein.

Figure 1:
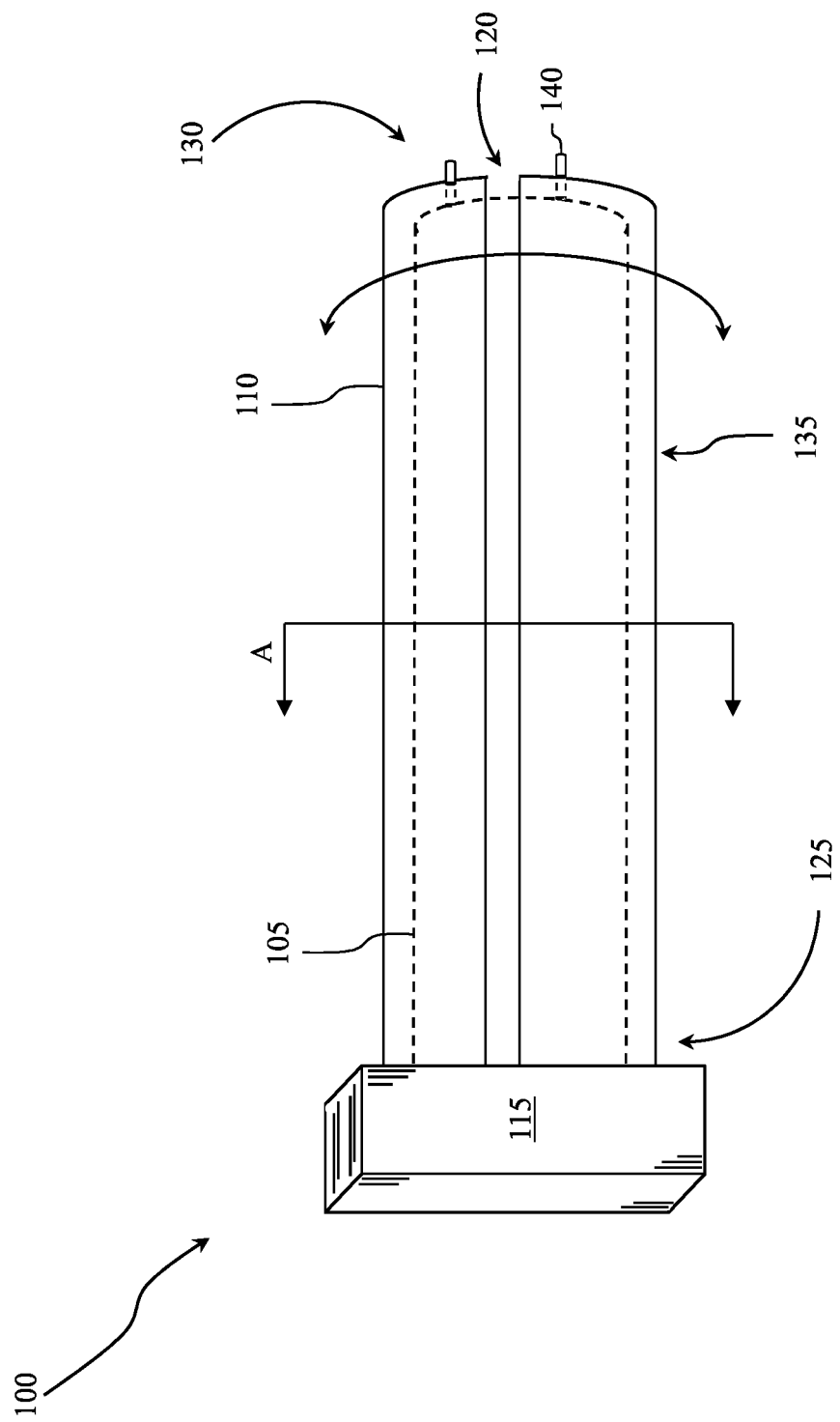
FIG. 1 illustrates a perspective view of a lighting assembly, according to some embodiments.

Unless otherwise specifically noted, articles depicted in the drawings are not necessarily drawn to scale.

DETAIL DESCRIPTIONS OF THE INVENTION

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or"

denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

Other technical advantages may become readily apparent to one of ordinary skill in the art after review of the following figures and description. It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Unless otherwise indicated, the drawings are intended to be read together with the specification and are to be considered a portion of the entire written description of this invention. As used in the following description, the terms "horizontal", "vertical", "left", "right", "up", "down" and the like, as well as adjectival and adverbial derivatives thereof (e.g., "horizontally", "rightwardly", "upwardly", "radially", etc.), simply refer to the orientation of the illustrated structure as the particular drawing figure faces the reader. Similarly, the terms "inwardly," "outwardly" and "radially" generally refer to the orientation of a surface relative to its axis of elongation, or axis of rotation, as appropriate. As used herein, the term "dorsal" refers to positions that are located near, on, or towards the upper or top side of a structure.

The present disclosure includes many aspects and features. Moreover, while many aspects and features relate to, and are described in the context of disinfecting and illuminating lighting assemblies, embodiments of the present disclosure are not limited to use only in this context.

With the onset of more deadly viruses and diseases such as COVID-19, it may be useful to set standards and equipment to sterilize constantly used surfaces and the air without having to manually clean them. With the SARS-CoV-2 virus, which is transmitted by airborne droplets, manual cleaning is not even possible. While there exists many precautions today such as with the use of sanitary wipes, antiviral sprays, and masks, it is still difficult to employ means of cleaning many surfaces simultaneously. Ultraviolet ("UV") light has often been used to disinfect items and surfaces such as cleaning water for drinking to sterilizing science lab equipment to the use of UV emitting handheld devices waved over items such as a phone.

Fluorescent bulbs, which are readily available and often times already installed as a light fixture in places such as restaurants and department stores, produce UV light but this is not usable for disinfection. Disinfecting UV lightbulbs are also available, though less widely used, but these are not suitable for illumination.

The instant disclosure seeks to provide lighting assemblies that selectively emit ultraviolet radiation and have rotatable sleeve assemblies. The instant disclosure seeks to provide lighting assemblies that use lightbulbs that emit ultraviolet ("UV") radiation and a sleeve that converts UV radiation to visible light. The instant disclosure further seeks to provide lighting assemblies that use motor one or more assemblies to rotate the sleeve and thereby selectively allow the lighting assemblies to emit UV radiation or visible light.

Figure 2:
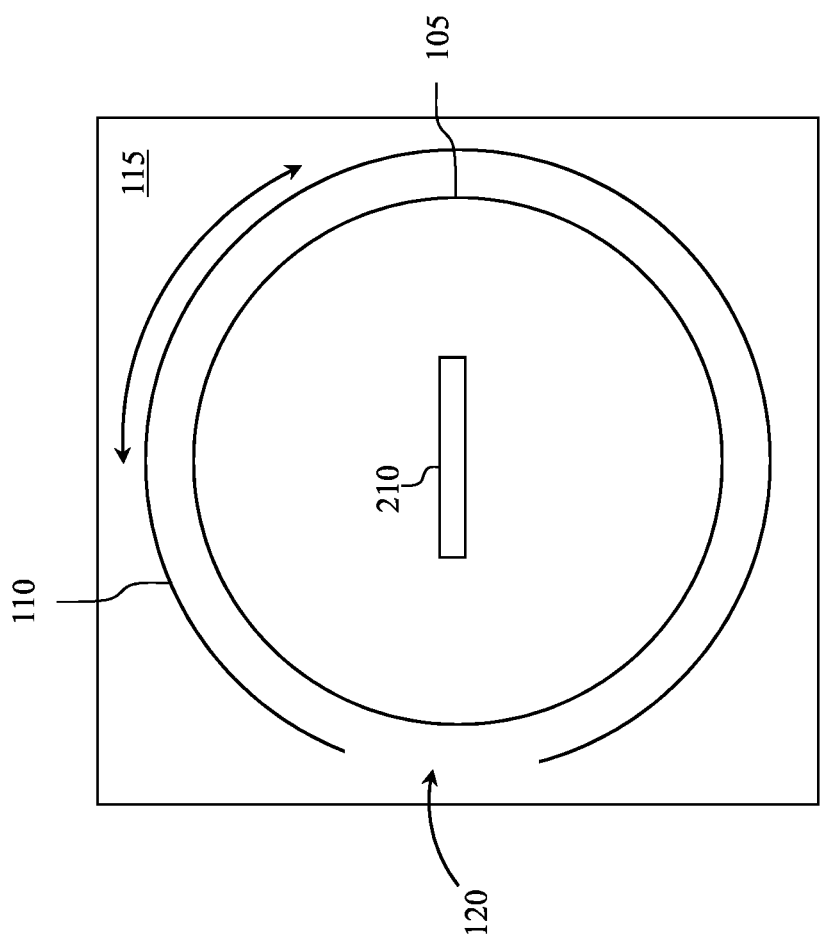
FIG. 2 illustrates View A of the lighting assembly of FIG. 1, according to other embodiments.

FIGS. 1-17 are used for the purpose of describing the embodiments of the instant disclosure and are not intended to be limiting. FIG. 1 depicts a lighting assembly, generally 100, in accordance with some embodiments. Lighting assembly 100 is a device that selectively emits UV radiation or visible light to disinfect or illuminate, respectively, surfaces (e.g., objects, counter tops, rooms, walls, floors, etc.), as depicted in FIG. 2. Applicable surface can also include, but are not limited to, the surface of bacterial cells and/or viral particles. As used herein, the term "disinfect" denotes the act of destroying or inactivating bacterial cells and/or viral particles. In preferred embodiments, the lighting assembly 100 includes a lightbulb 105, a sleeve 110, a power source 305, a motor assembly 115, and a communications device 310 all interconnected and communicatively coupled to a control circuit 300. In some embodiments, the lighting assembly 100 does not include the communications device 310 and must be operated manually. The power source 305 can be any type of device that supplies electricity in the proper format and voltage to facilitate one or more embodiments. The motor assembly 115 can include any number and/or types of motors that can facilitate one or more embodiments.

Figure 3:
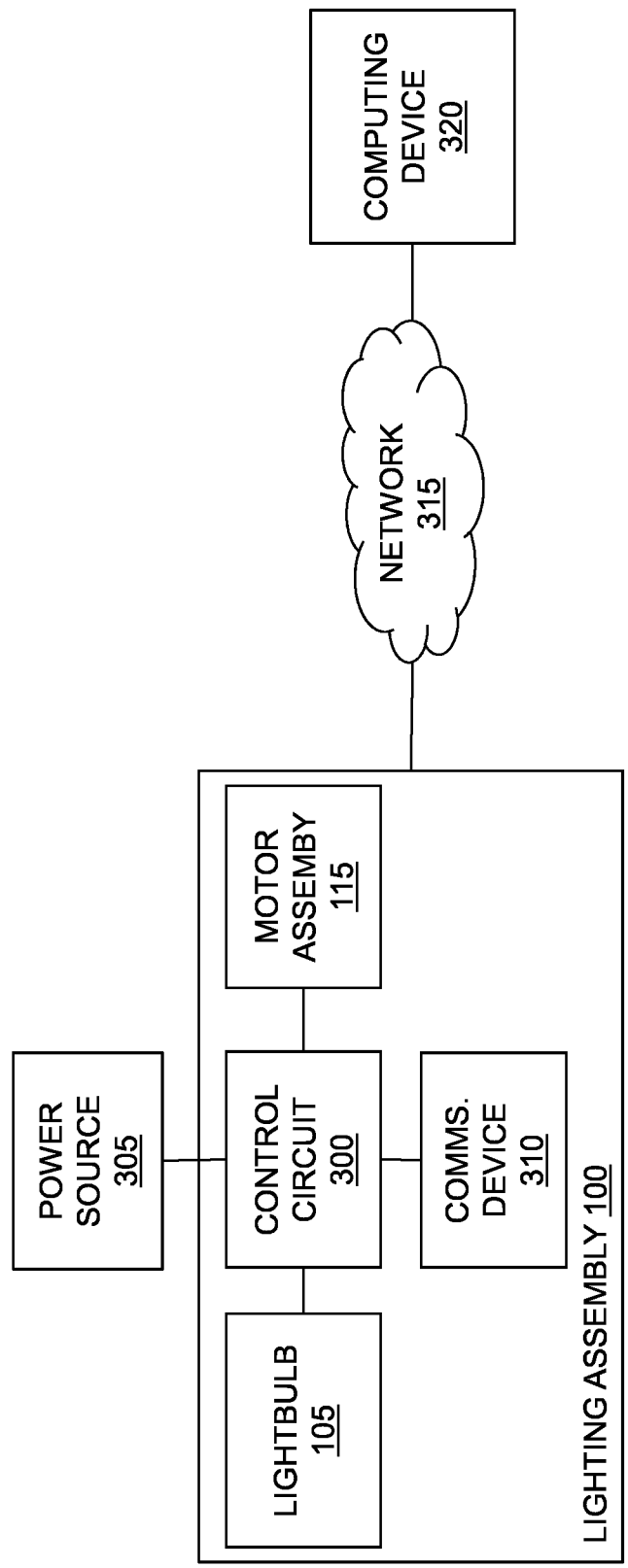
FIG. 3 illustrates a block diagram of a communications environment, according to certain embodiments.

The control circuit 300 is one or more devices that control the operation of the lighting assembly 100 (e.g., operation of the lightbulb 105 and the motor assembly 115). The control circuit 300 preferably includes a timer function that controls the flow of electricity to the lightbulb 105 and/or the motor assembly 115. For example, the timer function allows the control circuit 300 to activate the lightbulb 105 and/or the motor assembly 115 at one or more preset times (e.g., factory-defined times and/or user-defined times). FIG. 3 depicts a block diagram of a communications environment for the lighting assembly 100, according to some embodiments. The communications device 310 preferably allows the lighting assembly 100 to communicate with one or more computing devices 320 via network 315, which can be any combination of connections and protocols that support communications between the lighting assembly 100 and the computing device 320.

The computing device 320 can be a mobile device, desktop computing device, or similar computing device that users can utilize to control one or more functions and/or processes of the lighting assembly 100. For example, the computing device 320 can be a mobile device that controls the lighting assembly 100 via a mobile application ("app") that is associated with the lighting assembly 100. In other embodiments, the computing device 320 communicates directly with the lighting assembly 100 via IR communications. In general, the network 315 can be, for example, a local area network (LAN), a wide area network (WAN) such as the Internet, or a combination of the two, and can include wired, wireless, or fiber optic connections. In preferred embodiments, the control circuit 300 is configured to receive, via the communications device 310, operational instructions that instruct the lighting assembly 100 to assume the first state or the second state (discussed further below).

The lightbulb 105 is a cylindrically shaped lightbulb that emits UV radiation via the excitation of internal components (e.g., mercury vapor) using electrode 210. In general, the lightbulb 105 can have any shape and/or number of internal components to facilitate an embodiment of the instant disclosure. The lightbulb 105 includes an end 625 and end 630. Pins 140 are included on the end 625 and/or the end 630 either of which may be coupled to the motor assembly 115. In some embodiments, the lightbulb 105 is made of a clear glass that facilitates UV radiation transmission. In certain embodiments, the lightbulb, the lightbulb 105 is partially covered with a coating(s) that converts UV radiation to visible light (discussed further below in reference to FIGS. 11-16). A key component of the lighting assembly 100 is the sleeve 110, which includes a first coating 135 that converts UV radiation to visible light. The first coating 135 preferably includes one or more phosphors that emit visible light when exposed to UV radiation.

Figure 7:
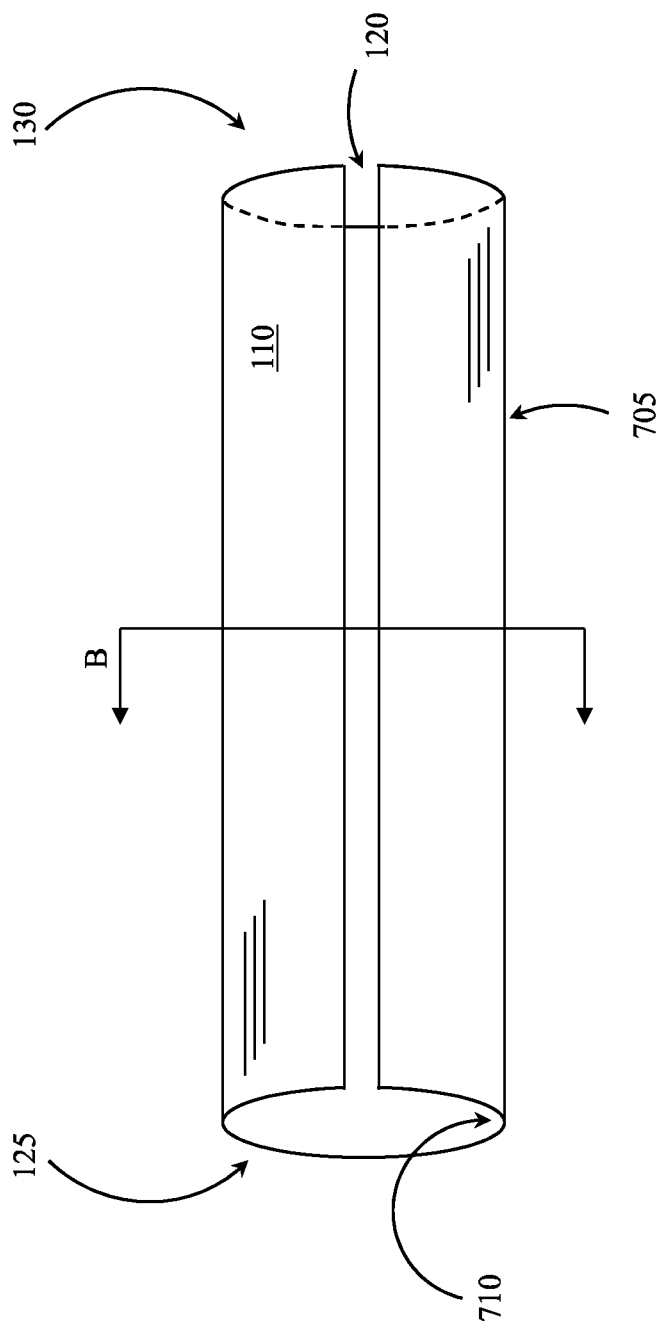
FIG. 7 illustrates a perspective view of a sleeve of the lighting assembly, according to certain embodiments.
Figure 8:
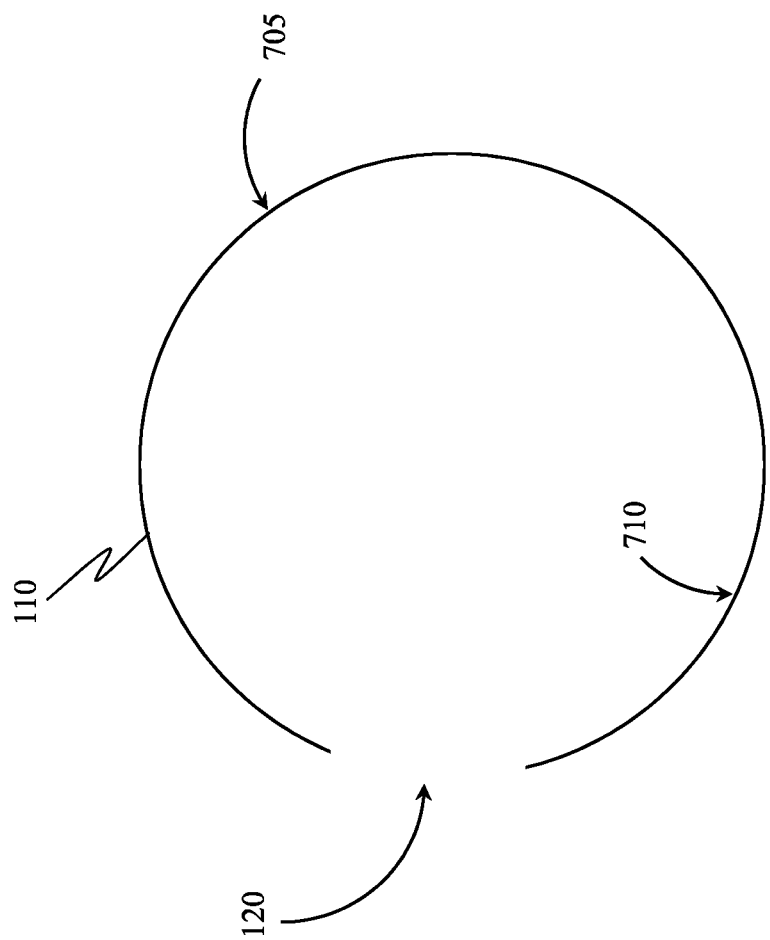
FIG. 8 illustrates View B of the sleeve of FIG. 7, according to yet still other embodiments.
Figure 9:
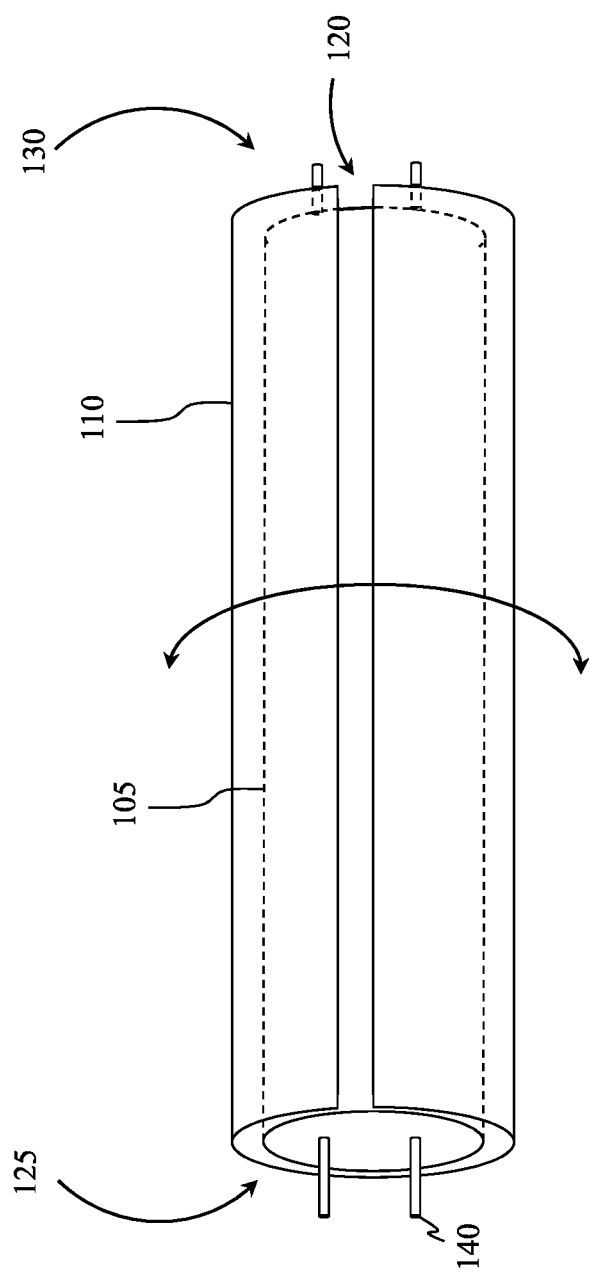
FIG. 9 illustrates the lightbulb positioned of FIG. 6 positioned within the sleeve of FIG. 7, according to some embodiments.

FIG. 7 depicts a perspective view of the sleeve 110, according to some embodiments. The sleeve 110 is a preferably a tubular structure that includes a first end 125, a second end 130, a first surface 705, and a second surface 710. Although the motor assembly is depicted as being mechanically coupled to the first end 125, the component can be mechanically coupled to the first end 125 and/or the second end 130. Although the sleeve 100 uses a coating to convert UV radiation to visible light, it also allows the allows UV radiation to pass through via slit 120, which traverses the sleeve 110 from the first end 125 to the second end 130. The coating can be applied to the first surface 705 and/or the second surface 710. In general, the slit 120 is a void in the sleeve 110 (or a void in the coating on the sleeve 110) that allows the UV radiation from the lightbulb 105 to pass through without being converted to visible light. In other words, the slit 120 is the key component that allows the lighting assembly 100 to selectively emit UV radiation or visible light The motor assembly 115 is mechanically coupled to the sleeve 110. The sleeve 110 is circumferentially positioned about the lightbulb 105. To rotate the component, the sleeve 110 is rotatably coupled to the lightbulb 105 via the motor assembly 115.

Figure 5:
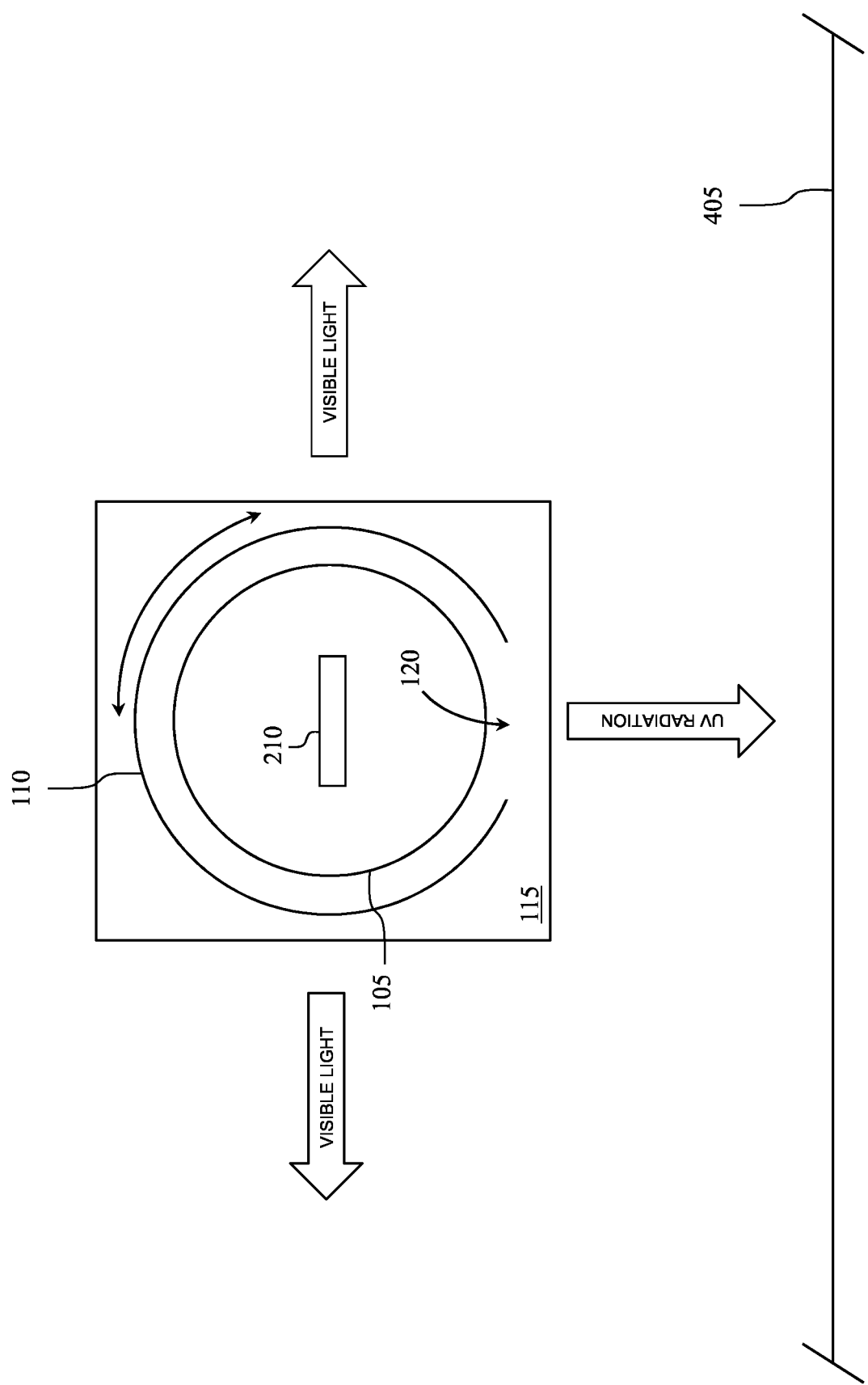
FIG. 5 illustrates an operational state of the lighting assembly, according to some embodiments.
Figure 6:
FIG. 6 illustrates a perspective view of a lightbulb of the lighting assembly, according to other embodiments.

The lighting assembly 100 is preferentially installed horizontally in a ceiling light fixture, which generally directs emissions laterally and downwards. As such, in these descriptions, we assume that all upward emissions are blocked by the light fixture to which the lighting assembly is attached. In other embodiments, the lighting assembly 100 is a stand-alone unit that does not require installation in to a ceiling light fixture for operation. The lighting assembly 100 can change its configurations to selectively emit UV radiation or visible light to disinfect or illuminate a surface, respectively. For example, the motor assembly 115 selectively rotates the sleeve 110 about the lightbulb 105 and thereby positions the lighting assembly 100 in a first state or a second state. As depicted in FIG. 5, in the first state, the lighting assembly 100 emits UV radiation towards a surface 405, which represents any surface that requires disinfection or illumination. Here, the sleeve 110 is coated with the first coating 135, which blocks UV radiation emissions from the lightbulb 105. Specifically, in the first state, the motor assembly 115 orients the slit 120 towards the surface 405 and thereby directs the UV radiation towards the surface 405 while the rest of the sleeve 110 emits visible light produced via the first coating 135.

Figure 4:
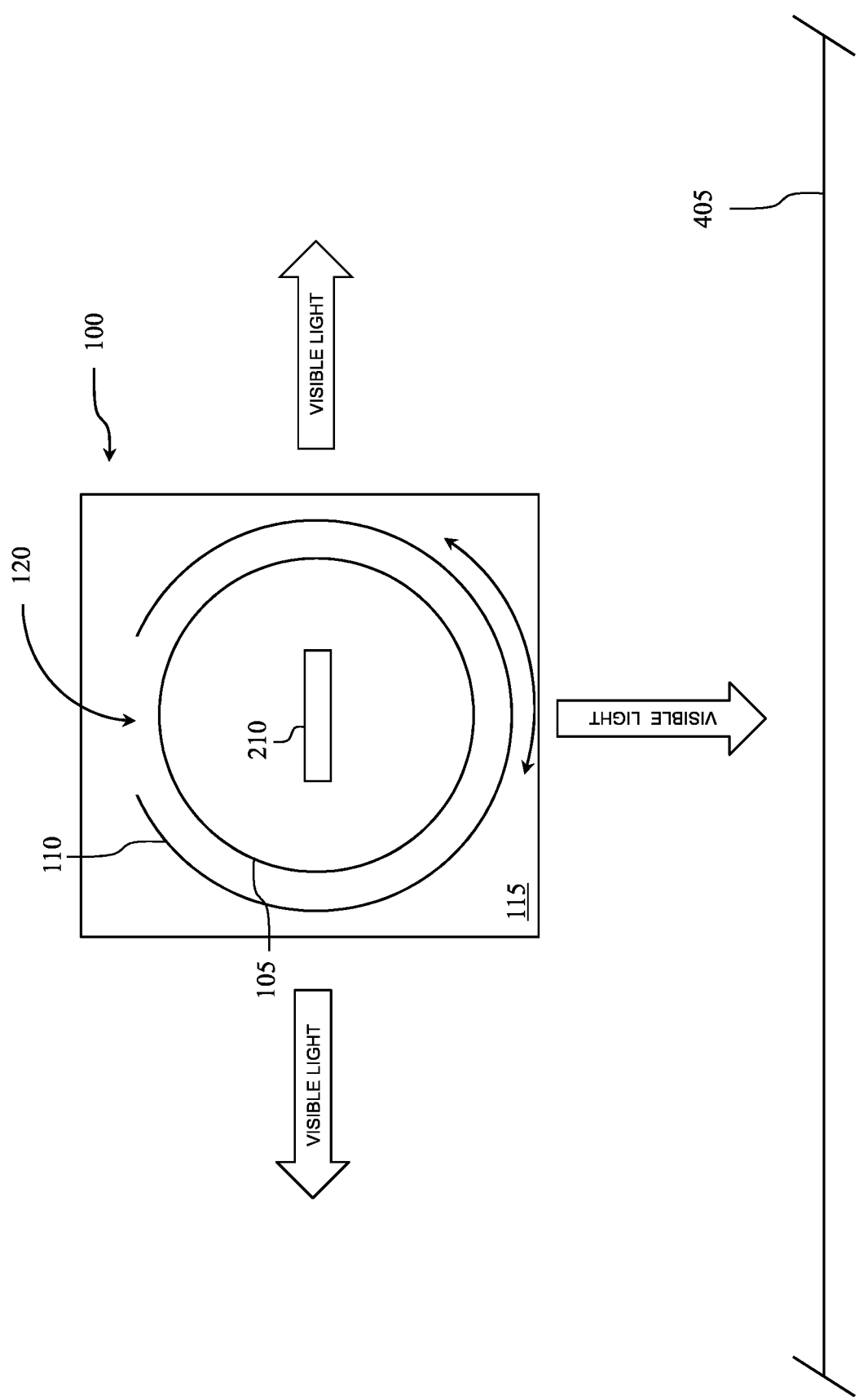
FIG. 4 illustrates an operational state of the lighting assembly, according to yet still other embodiments.

As depicted in FIG. 4, in the second state, the lighting assembly 100 emits visible light towards the surface 405. Here, in the second state, the sleeve 110 is coated as discussed above, and the motor assembly 115 orients the slit 120 away from the surface 405, which thereby directs UV radiation emissions of the lightbulb 105 away from the surface 405 and simultaneously directs visible light towards the surface 405.

Figure 10:
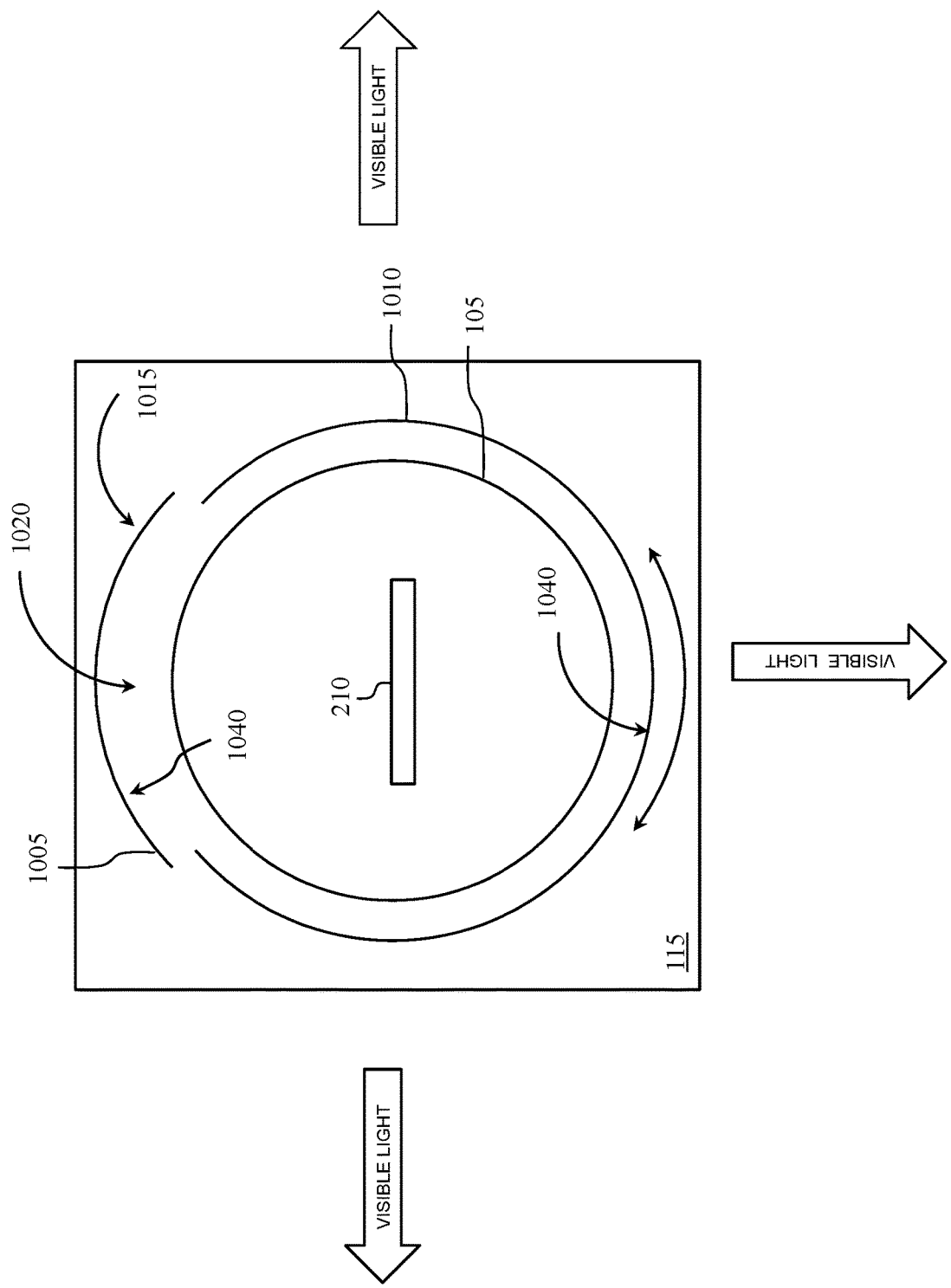
FIG. 10 illustrates a side cut-through view of an operational state of a lighting assembly, according to other embodiments.

Slit structures that function similar to the slit 120 (i.e., selectively allow the passage of UV radiation) can be achieved using various solutions. FIG. 10 depicts side cut-through of the lighting assembly 100 that is similar to the orientation of View A (discussed above), in accordance with certain embodiments. Here, the sleeve 110 includes a first sleeve portion 1005 and a second sleeve portion 1010. The second sleeve portion 1010 includes a slit 1020, which functions similarly to the slit 120. The first sleeve portion 1005 and the second sleeve portion 1010 are each circumferentially positioned about the lightbulb 105, wherein the first sleeve portion 1005 is circumferentially smaller compared to the second sleeve portion 1010.

In other words, the first sleeve portion 1005 has a shorter arc length than the second sleeve portion 1010. The first sleeve portion 1005 and the second sleeve portion 1010 each include a coating that converts UV to visible light. The first sleeve portion 1005 and the second sleeve portion 1010 include the second coating 1015 and the third coating 1040, respectively, that function similarly to the first coating 135. The first sleeve portion 1005 is preferably coupled to the motor assembly 115. The second sleeve portion 1010 is mechanically coupled to the motor assembly 115. During operation, the motor assembly 115 holds the first sleeve portion 1005 stationary and circumferentially rotates the second sleeve portion 1010 about the lightbulb 105. In the first state, the motor assembly 115 orients the slit 1020 to not overlap with the first sleeve portion 1005 and thereby directs the UV radiation from the lightbulb 105 towards a surface (not shown). In the second state, the motor assembly 115 orients the slit 1020 to overlap with the first sleeve portion 1010 and thereby directs the UV radiation from the lightbulb 105 away from the surface and simultaneously directs visible light towards the surface.

Figure 11:
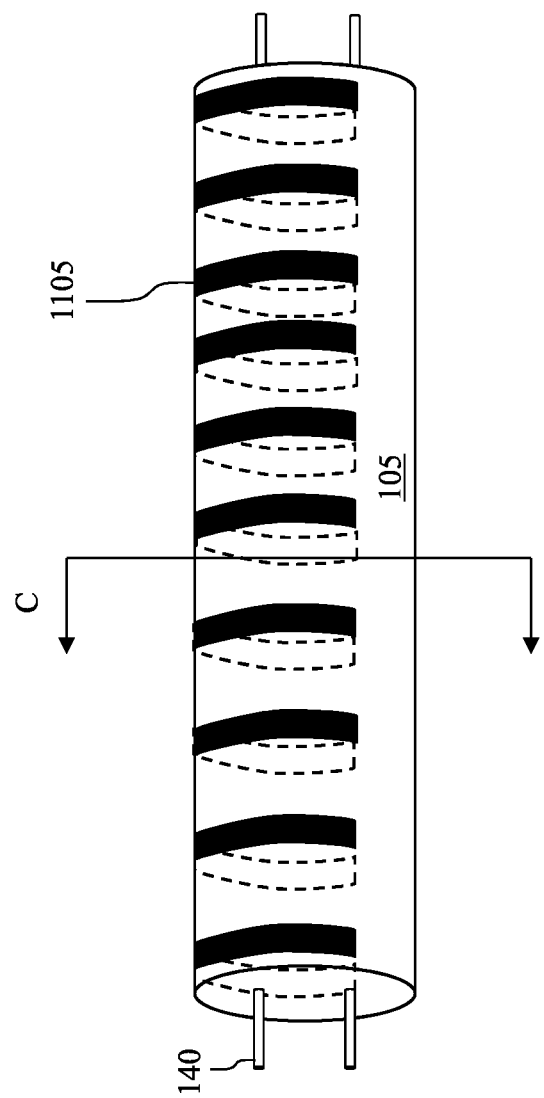
FIG. 11 illustrates a perspective view of the lightbulb of FIG. 6 coated with stripes, according to certain embodiments.
Figure 12:
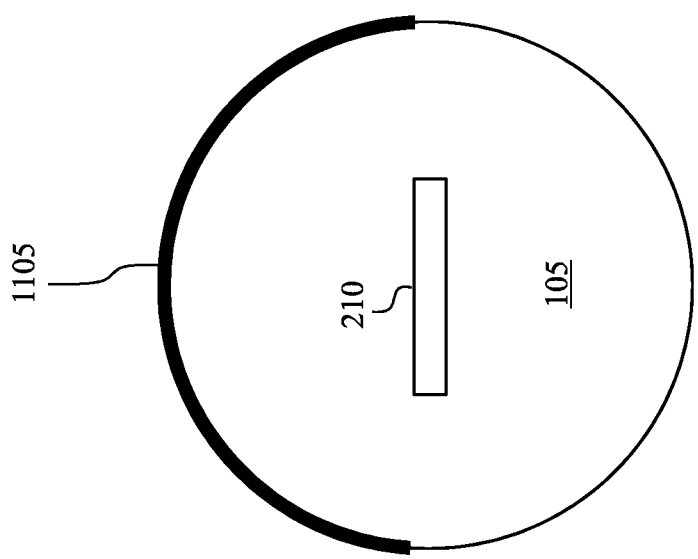
FIG. 12 illustrates View C of the lightbulb of FIG. 11, according to yet still other embodiments.
Figure 13:
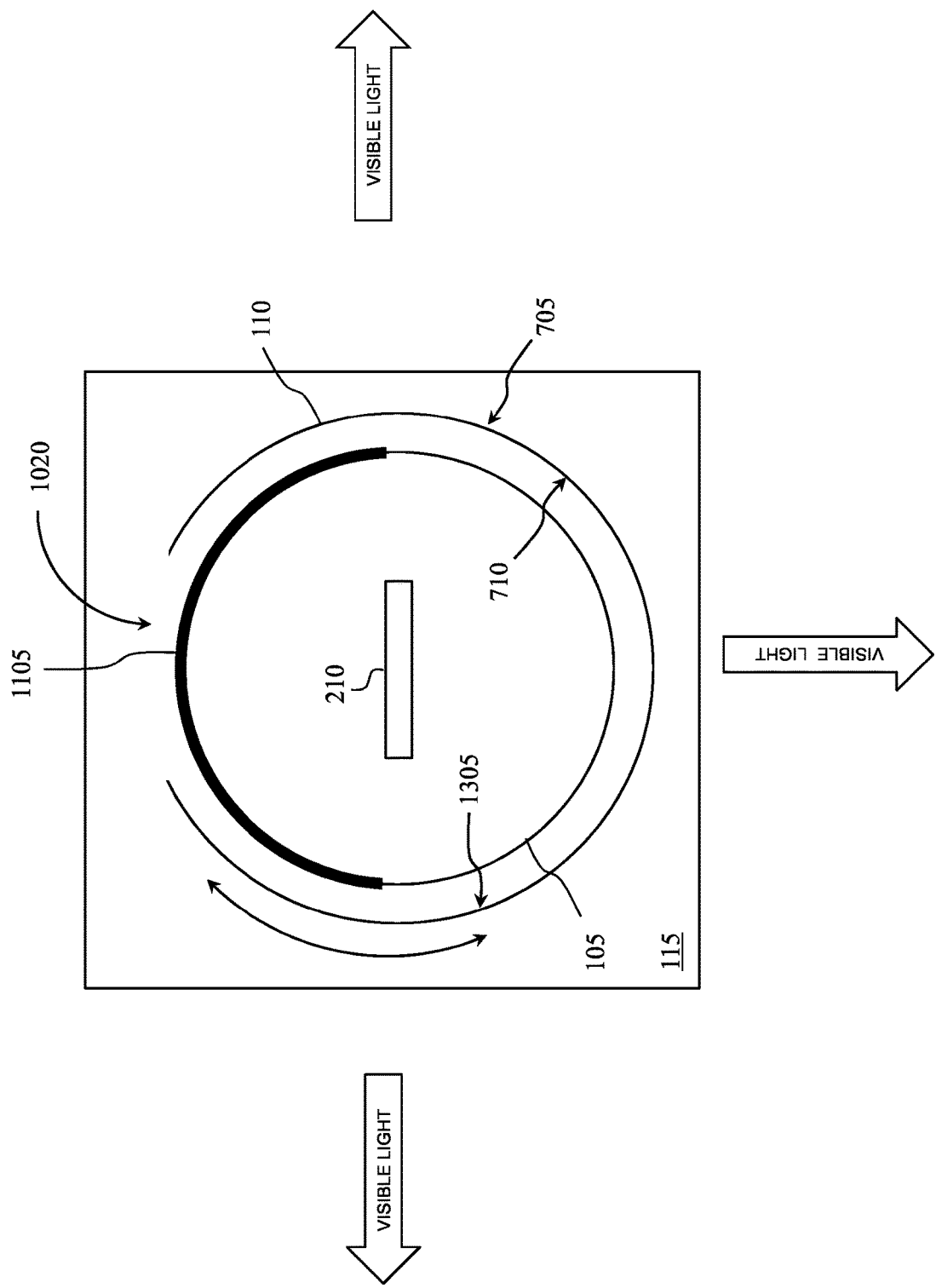
FIG. 13 illustrates a side cut-through view of an operational state of a lighting assembly, according to some embodiments.
Figure 14:
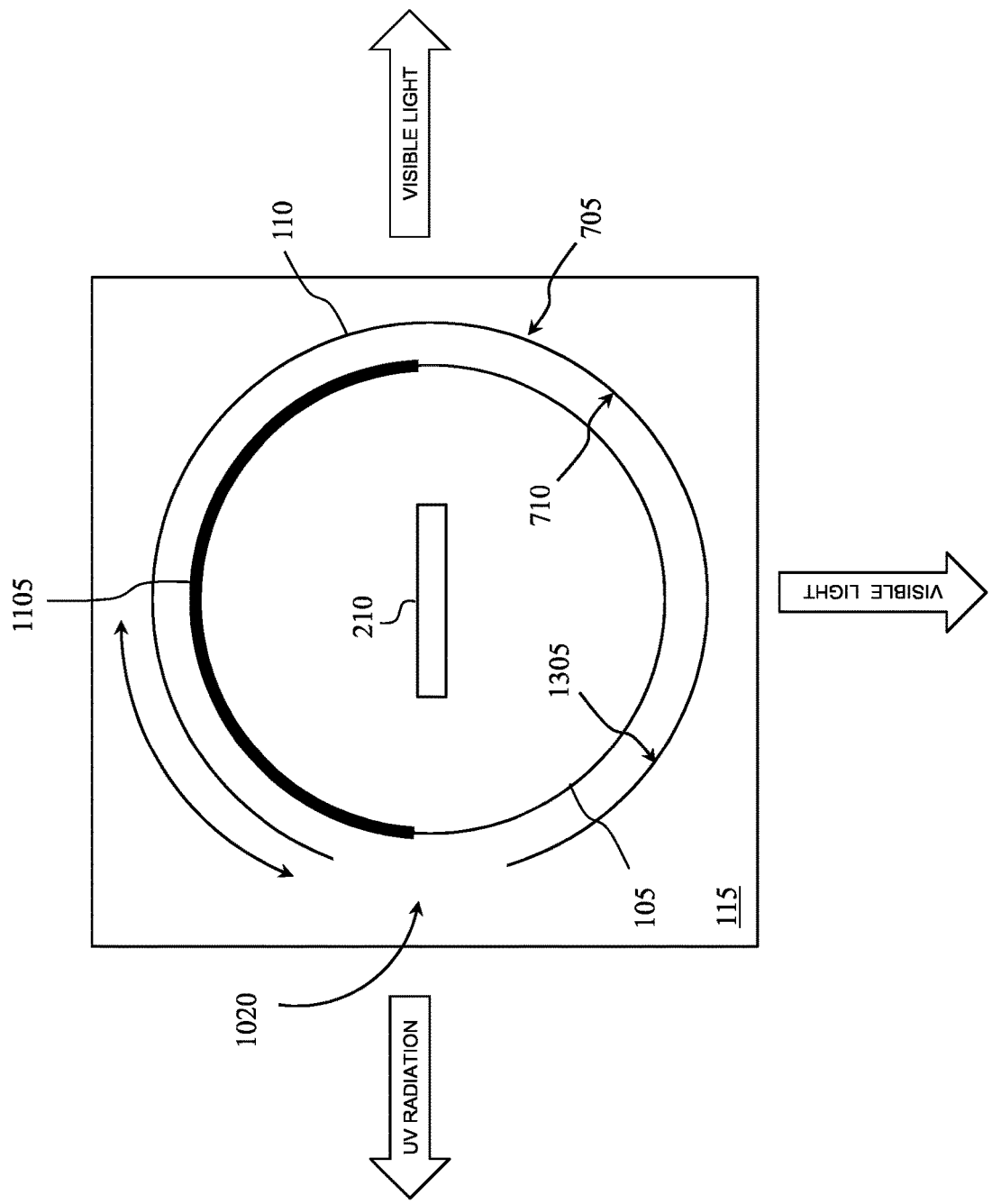
FIG. 14 illustrates a side cut-through view of an operational state of the lighting assembly of FIG. 13, according to other embodiments.

FIGS. 11-14 depict an alternative embodiment of the lighting assembly 100 that uses a slit structure that functions similar to the slit 120 (i.e., selectively allow the passage of UV radiation). Here, the lighting assembly 100 includes the sleeve 110 and the lightbulb 105, which further includes a fourth coating 1105. The sleeve 110 includes the fifth coating 1305, which is similar to the first coating 135. The fourth coating 1105 converts UV radiation to visible light similar to the first coating 135. The coatings of the instant disclosure convert UV radiation to visible light using one or more phosphors. The fourth coating 1105 is present in the form of stripes that only cover half of the circumference of the lightbulb 105 (as depicted in FIG. 11-12) and thereby asymmetrically cover the light bulb 105. The stripes of the fourth coating 1105 are longitudinally positioned on the lightbulb 105. As depicted in FIG. 14, in the first state, the motor assembly 115 orients the slit 1020 to not overlap the fourth coating 1105 and thereby directs UV radiation towards a surface (not depicted). As depicted in FIG. 13, in the second state, the motor assembly 115 orients the slit 1020 to overlap the fourth coating 1105 and thereby directs UV radiation emissions away from the surface and simultaneously directs visible light towards the surface.

Figure 15:
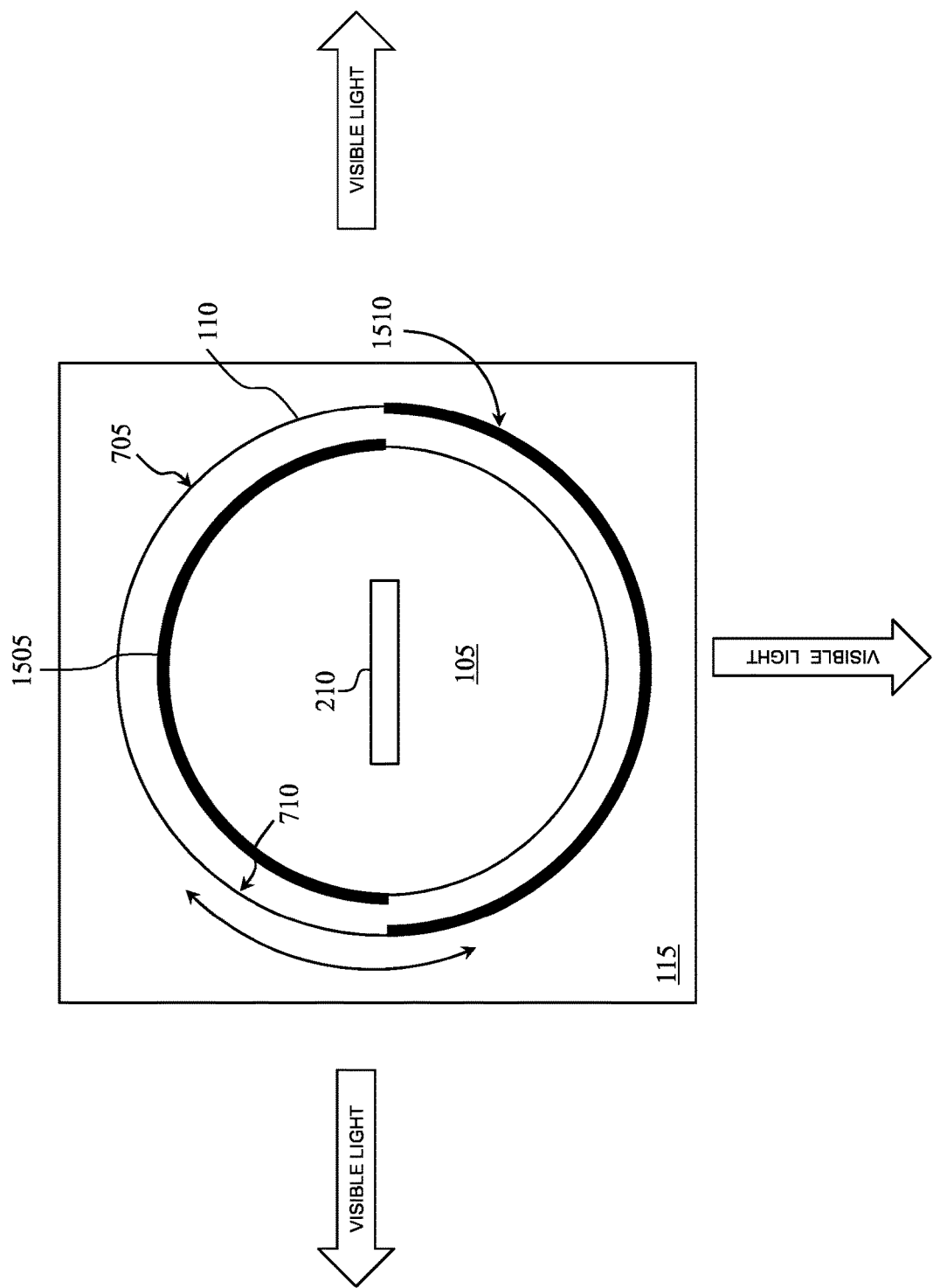
FIG. 15 illustrates a side cut-through view of an operational state of a lighting assembly, according to certain embodiments.
Figure 16:
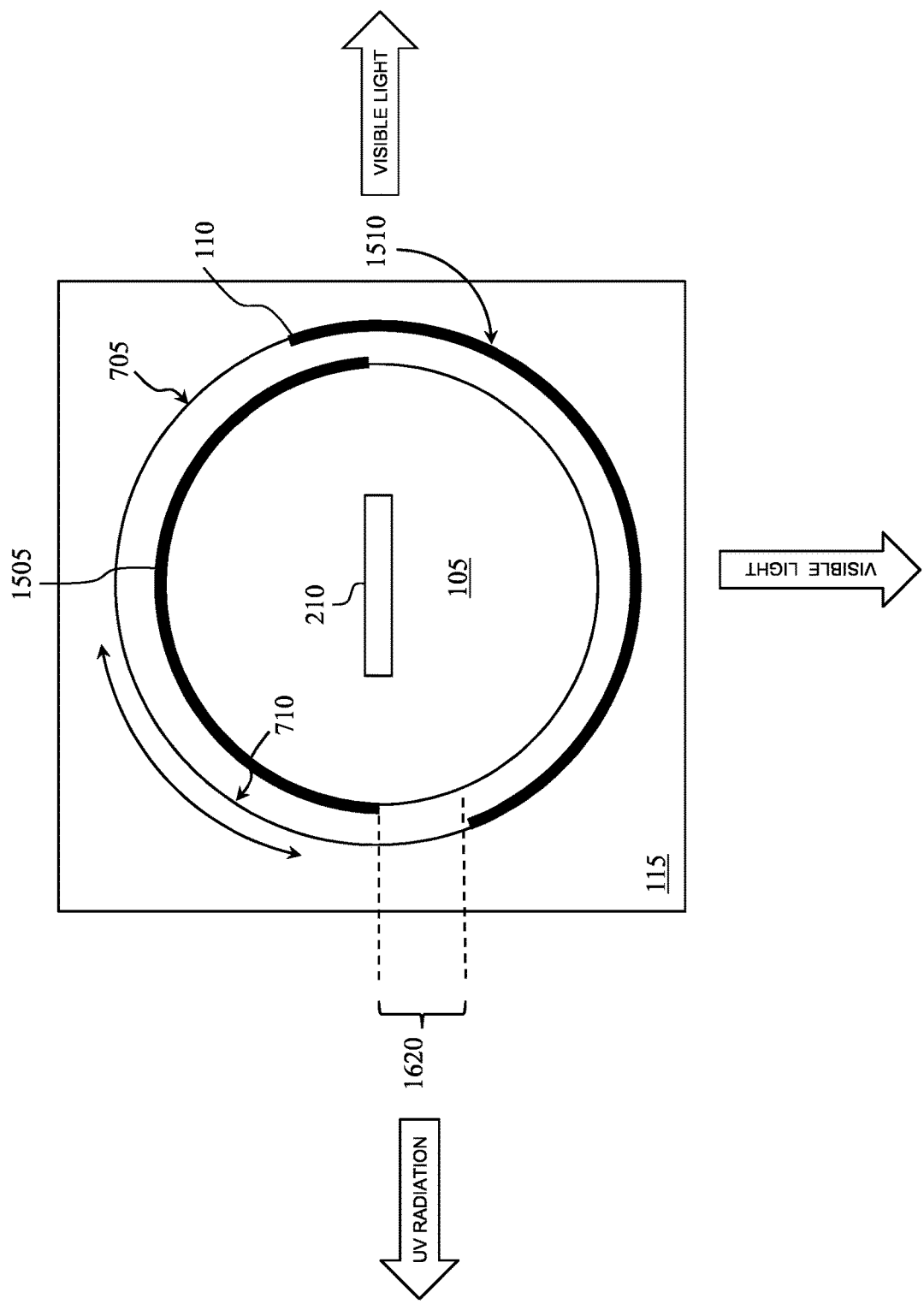
FIG. 16 illustrates a side cut-through view of an operational state of the lighting assembly of FIG. 15, according to yet still other embodiments.
Figure 17:
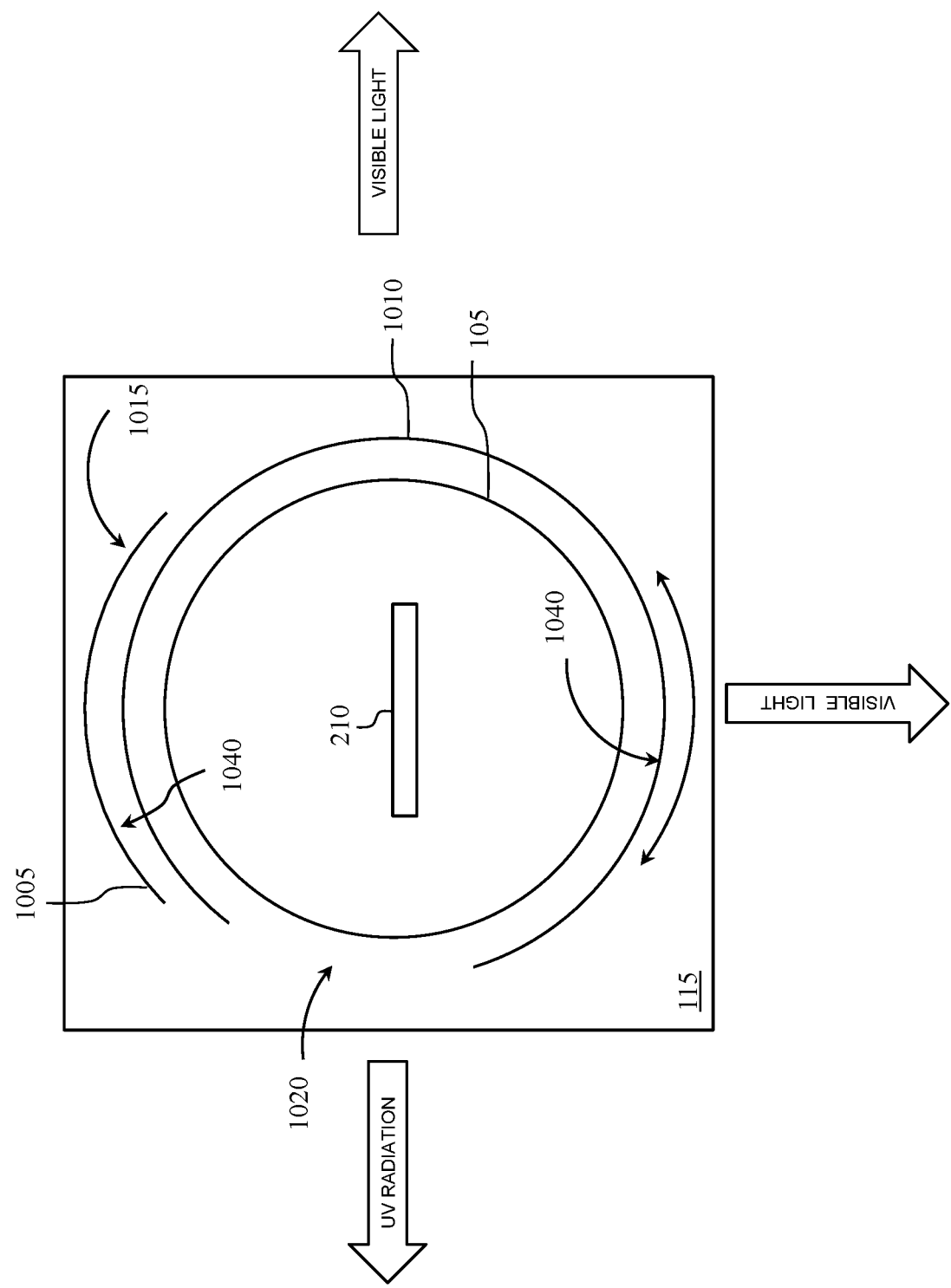
FIG. 17 illustrates a side cut-through view of an operational state of the lighting assembly of FIG. 10, according to yet still other embodiments.

FIGS. 15-16 depict a side-cut through view (similar to the orientation of View A) of an alternative embodiment of the lighting assembly 100 that uses a slit structure that functions similar to the slit 120 (i.e., selectively allow the passage of UV radiation). Here, the lighting assembly 100 includes the sleeve 110 and the lightbulb 105, which further includes a fourth coating 1105 that converts UV radiation to visible light. Here, the sleeve 110 does not include the slit 120. The sleeve 110 includes a seventh coating 1510, which is longitudinally positioned on half of the sleeve 110 and extends from the first end 125 to the second end 130. Similar to the first coating 135, the seventh coating includes a phosphor(s) and converts UV radiation to visible light.

The lightbulb includes a sixth coating 1505, which converts UV radiation to visible light similar to the first coating 135. Here, the sixth coating 1505 and the seventh coating 1510 together form a structure that is functionally similar the slit 120. The sixth coating 1505 is present in the form of a strip that is longitudinally positioned on the lightbulb 105. Here, in the first state, the motor assembly 115 rotates the sleeve 110 to orient the seventh coating 1510 oblique or perpendicular to the sixth coating 1505 and thereby form a second slit 1620 through which UV radiation emits towards a surface (not shown). In the second state, the motor assembly 115 rotates the sleeve 110 to orient the seventh coating 1510 co-planar to the sixth coating 1505 in a non-overlapping manner and thereby direct visible light towards the surface.

Although the disclosure has been explained in relation to its preferred embodiment, it is to be understood that many other possible modifications and variations can be made without departing from the spirit and scope of the disclosure.

What is claimed is:

1. A lighting assembly, comprising:
   a lightbulb;
   a sleeve;
   a motor assembly;
   a control circuit;
   a power source;
   a first state;
   a second state;
   wherein
     the control circuit is communicatively coupled to the power source, the lightbulb, and the motor assembly;
     the lightbulb emits ultra violet ("UV") radiation;
     the sleeve
       converts UV radiation to visible light;
       is circumferentially positioned about the lightbulb;
       is rotatably coupled to the lightbulb via the motor assembly;
     the motor assembly
       is mechanically coupled to the sleeve;
       selectively rotates the sleeve about the lightbulb and thereby positions the lighting assembly in the first state or the second state;
     in the first state, the lighting assembly emits UV radiation towards a surface;
     in the second state, the lighting assembly emits visible light towards the surface;
     the sleeve comprises:
       a slit;
       a first end;
       a second end;
       a first surface;
       a second surface;
       a first coating
       a first sleeve portion and a second sleeve portion;
     the slit longitudinally traverses the sleeve;
     the slit traverses the sleeve from the first end to the second end;
     in the first state, the motor assembly orients the slit towards the surface and thereby directs UV radiation emissions towards the surface;
     in the second state, the motor assembly orients the slit away from the surface, which thereby directs UV radiation emissions away from the surface and simultaneously directs visible light towards the surface;
     wherein the lightbulb is cylindrically shaped;
     the motor assembly is mechanically coupled to one or more of the first end and the second end;
     the first coating converts UV radiation to visible light;
     the first coating comprises a phosphor;
     the first sleeve portion and the second sleeve portion are each circumferentially positioned about the lightbulb;
     the first sleeve portion and the second sleeve portion each convert UV to visible light
     the first sleeve portion is circumferentially smaller compared to the second sleeve portion;
     the first sleeve portion is coupled to the motor assembly;
     the second sleeve portion is mechanically coupled to the motor assembly;
     the motor assembly holds the first sleeve stationary and circumferentially rotates the second sleeve portion about the lightbulb;
     in the first state, the motor assembly orients the slit to not overlap the first sleeve portion and thereby directs UV radiation towards the surface; and
     in the second state, the motor assembly orients the slit to overlap the first sleeve portion and thereby directs UV radiation emissions away from the surface and simultaneously directs visible light towards the surface.

2. The lighting assembly of claim 1, further comprising:
   a communications device that facilitates wireless communications;
   wherein
     the communications device is communicatively coupled to the control circuit; and
     the control circuit is configured to receive, via the communications device, operational instructions that instruct the lighting assembly to assume the first state or the second state.

3. A lighting assembly, comprising:
   a lightbulb;
   a sleeve;
   a motor assembly;
   a control circuit;
   a power source;
   a first state;
   a second state;
   wherein
     the control circuit is communicatively coupled to the power source, the lightbulb, and the motor assembly;
     the lightbulb emits UV radiation;
     the sleeve
       converts UV radiation to visible light;
       is circumferentially positioned about the lightbulb;
       is rotatably coupled to the lightbulb via the motor assembly;

comprises a slit the longitudinally traverses the sleeve the motor assembly;
is mechanically coupled to the sleeve;
selectively rotates the sleeve about the lightbulb and thereby positions the lighting assembly in the first state or the second state;
in the first state, the lighting assembly emits UV radiation towards a surface;
in the second state, the lighting assembly emits visible light towards the surface;

the sleeve comprises:
a first end;
a second end;
a first surface;
a second surface;
a fifth coating;

the motor assembly is mechanically coupled to one or more of the first end and the second end;

the slit traverses the sleeve from the first end to the second end;

the fifth coating:
comprises a phosphor; and
converts UV radiation to visible light;

wherein the lightbulb comprises a fourth coating;
the fourth coating converts UV radiation to visible light;
the fourth coating is in the form of stripes;
the stripes asymmetrically cover the light bulb;
in the first state, the motor assembly orients the slit to not overlap the fourth coating and thereby directs UV radiation emissions towards a surface; and
in the second state, the motor assembly orients the slit to overlap the fourth coating and thereby directs UV radiation emissions away from the surface and simultaneously directs visible light towards the surface.

\* \* \* \* \*